US006778860B2

(12) United States Patent
Ostroff et al.

(10) Patent No.: US 6,778,860 B2
(45) Date of Patent: Aug. 17, 2004

(54) SWITCHED CAPACITOR DEFIBRILLATION CIRCUIT

(75) Inventors: Alan H. Ostroff, San Clemente, CA (US); Gary R. Mezack, Norco, CA (US)

(73) Assignee: Cameron Health, Inc., San Clemente, CA (US)

( * ) Notice: Subject to any disclaimer, the term of this patent is extended or adjusted under 35 U.S.C. 154(b) by 0 days.

(21) Appl. No.: 10/011,952

(22) Filed: Nov. 5, 2001

(65) Prior Publication Data

US 2003/0088281 A1 May 8, 2003

(51) Int. Cl.[7] .................................................. A61N 1/39
(52) U.S. Cl. ................................................ 607/70; 607/5
(58) Field of Search ............................ 607/4, 5, 7, 11, 607/9, 68, 70, 72, 74

(56) References Cited

U.S. PATENT DOCUMENTS

| 3,653,387 A | 4/1972 | Ceier |
| 3,710,374 A | 1/1973 | Kelly |
| 3,911,925 A | 10/1975 | Tillery, Jr. |
| 4,157,720 A | 6/1979 | Greatbatch |
| 4,191,942 A | 3/1980 | Long |

(List continued on next page.)

FOREIGN PATENT DOCUMENTS

| DE | 298 01 807 U1 | 7/1998 |
| EP | 0 095 727 A1 | 12/1983 |
| EP | 0 316 616 A2 | 5/1989 |
| EP | 0 316 616 A3 | 5/1989 |
| EP | 0 347 353 A1 | 12/1989 |

(List continued on next page.)

OTHER PUBLICATIONS

U.S. patent application Ser. No. 09/663,607 to Gust H. Bardy et al., filed Sep. 18, 2000.
Friedman, Richard A. et al., "Implantable Defibrillators In Children: From Whence to Shock," *Journal of Cardiovascular Electrophysiology*, vol. 12, No. 3, Mar. 2001, pp. 361–362.
Gradaus, Rainer et al., "Nonthoracotomy Implantable Cardioverter Defibrillator Placement in Children: Use of Subcutaneous Array Leads and Abdominally Placed implantable Cardioverter Defibrillators in Children," *Journal of Cardiovascular Electrophysiology*, vol. 12, No. 3, Mar. 2001, pp. 356–360.
Mirowski, M. et al., "Automatic Detection and Defibrillation of Lethal Arrhythmias—A New Concept," *JAMA*, vol. 213, No. 4, Jul. 27, 1970, pp. 615–616.
Olson, Walter H. et al., "Onset and Stability for Ventricular Tachyarrhythmia Detection in an Implantable Pacer–Cardioverter–Defribrillator," IEEE, (1987) pp. 167–170.
Schuder, John C., "Completely Implanted Defibrillator," *JAMA*, vol. 214, No. 6, Nov. 9, 1970. p. 1123 (single sheet).
Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95–124.

(List continued on next page.)

*Primary Examiner*—George R. Evanisko
(74) *Attorney, Agent, or Firm*—Crompton, Seager & Tufte, LLC

(57) ABSTRACT

A defibrillator circuit for generating a rectangular waveform across a patient from capacitively stored energy and employing a plurality of capacitors initially chargeable to a common voltage and thereafter sequentially switchable into parallel relation with one another so as to raise the voltage supplied to an H-bridge circuit from a point of decay back to said common voltage.

4 Claims, 2 Drawing Sheets

U.S. PATENT DOCUMENTS

| | | |
|---|---|---|
| 4,223,678 A | 9/1980 | Langer et al. |
| 4,248,237 A | 2/1981 | Kenny |
| 4,291,707 A | 9/1981 | Heilman et al. |
| 4,314,095 A | 2/1982 | Moore et al. |
| 4,402,322 A | 9/1983 | Duggan |
| 4,407,288 A | 10/1983 | Langer et al. |
| 4,424,818 A | 1/1984 | Doring et al. |
| 4,450,527 A | 5/1984 | Sramek |
| 4,567,900 A | 2/1986 | Moore |
| 4,602,637 A | 7/1986 | Elmqvist et al. |
| 4,603,705 A | 8/1986 | Speicher et al. |
| 4,693,253 A | 9/1987 | Adams |
| 4,765,341 A | 8/1988 | Mower et al. |
| 4,800,883 A | 1/1989 | Winstrom |
| 4,830,005 A | 5/1989 | Woskow |
| 4,944,300 A | 7/1990 | Saksena |
| 5,105,810 A | 4/1992 | Collins et al. |
| 5,109,842 A | 5/1992 | Adinolfi |
| 5,129,392 A | 7/1992 | Bardy et al. |
| 5,133,353 A | 7/1992 | Hauser |
| 5,144,946 A | 9/1992 | Weinberg et al. |
| 5,184,616 A | 2/1993 | Weiss |
| 5,191,901 A | 3/1993 | Dahl et al. |
| 5,203,348 A | 4/1993 | Dahl et al. |
| 5,230,337 A | 7/1993 | Dahl et al. |
| 5,255,692 A | 10/1993 | Neubauer et al. |
| 5,261,400 A | 11/1993 | Bardy |
| 5,300,106 A | 4/1994 | Dahl et al. |
| 5,331,966 A | 7/1994 | Bennett et al. |
| 5,342,407 A | 8/1994 | Dahl et al. |
| 5,366,496 A | 11/1994 | Dahl et al. |
| 5,376,103 A | 12/1994 | Anderson et al. |
| 5,376,104 A | 12/1994 | Sakai et al. |
| 5,385,574 A | 1/1995 | Hauser et al. |
| 5,391,200 A | 2/1995 | KenKnight et al. |
| 5,405,363 A | 4/1995 | Kroll et al. |
| 5,411,539 A | 5/1995 | Neisz |
| 5,411,547 A | 5/1995 | Causey, III |
| 5,413,591 A | 5/1995 | Knoll |
| 5,423,326 A | 6/1995 | Wang et al. |
| 5,476,503 A | 12/1995 | Yang |
| 5,479,503 A | 12/1995 | Fujiwara |
| 5,507,781 A * | 4/1996 | Kroll et al. ................ 607/7 |
| 5,509,923 A | 4/1996 | Pyka et al. |
| 5,509,928 A | 4/1996 | Acken |
| 5,531,765 A | 7/1996 | Pless |
| 5,531,766 A | 7/1996 | Kroll et al. |
| 5,534,019 A | 7/1996 | Paspa |
| 5,534,022 A | 7/1996 | Hoffmann et al. |
| 5,597,956 A | 1/1997 | Ito et al. |
| 5,601,607 A | 2/1997 | Adams |
| 5,603,732 A | 2/1997 | Dahl et al. |
| 5,618,287 A | 4/1997 | Fogarty et al. |
| 5,620,477 A | 4/1997 | Pless et al. |
| 5,643,328 A | 7/1997 | Cooke et al. |
| 5,645,586 A | 7/1997 | Meltzer |
| 5,658,317 A | 8/1997 | Haefner et al. |
| 5,658,321 A | 8/1997 | Fayram et al. |
| 5,674,260 A | 10/1997 | Weinberg |
| 5,690,648 A | 11/1997 | Howell et al. |
| 5,690,683 A | 11/1997 | Haefner et al. |
| 5,697,953 A | 12/1997 | Kroll et al. |
| 5,713,926 A | 2/1998 | Hauser et al. |
| 5,766,226 A | 6/1998 | Pedersen |
| 5,776,169 A | 7/1998 | Schroeppel |
| 5,814,090 A | 9/1998 | Latterell et al. |
| 5,836,976 A | 11/1998 | Min et al. |
| 5,843,132 A | 12/1998 | Ilvento |
| 5,895,414 A | 4/1999 | Sanchez-Zambrano |
| 5,919,211 A | 7/1999 | Adams |
| 5,919,222 A | 7/1999 | Hjelle et al. |
| 5,925,069 A | 7/1999 | Graves et al. |
| 5,935,154 A | 8/1999 | Westlund |
| 5,941,904 A | 8/1999 | Johnston et al. |
| 6,014,586 A | 1/2000 | Weinberg et al. |
| 6,026,325 A | 2/2000 | Weinberg et al. |
| 6,058,328 A | 5/2000 | Levine et al. |
| 6,093,173 A | 7/2000 | Balceta et al. |
| 6,095,987 A | 8/2000 | Shmulewitz et al. |
| H1905 H | 10/2000 | Hill |
| 6,128,531 A | 10/2000 | Campbell-Smith |
| 6,144,866 A | 11/2000 | Miesel et al. |
| 6,144,879 A | 11/2000 | Gray |
| 6,185,450 B1 | 2/2001 | Seguine et al. |
| 6,241,751 B1 * | 6/2001 | Morgan et al. ................ 607/8 |
| 6,266,567 B1 | 7/2001 | Ishikawa et al. |
| 6,280,462 B1 | 8/2001 | Hauser et al. |
| 6,411,844 B1 | 6/2002 | Kroll et al. |
| 6,647,292 B1 | 11/2003 | Bardy et al. |
| 2001/0027330 A1 | 10/2001 | Sullivan et al. |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0107549 A1 | 8/2002 | Bardy et al. |

FOREIGN PATENT DOCUMENTS

| | | |
|---|---|---|
| EP | 0 517 494 B1 | 12/1992 |
| EP | 0 517 494 A3 | 12/1992 |
| EP | 0 518 599 B1 | 12/1992 |
| EP | 0 518 599 A2 | 12/1992 |
| EP | 0 536 873 B1 | 4/1993 |
| EP | 0 536 873 A1 | 4/1993 |
| EP | 0 586 858 B1 | 3/1994 |
| EP | 0 627 237 B1 | 12/1994 |
| EP | 0 627 237 A1 | 12/1994 |
| EP | 0 641 573 A2 | 3/1995 |
| EP | 0 641 573 A3 | 3/1995 |
| EP | 0 677 301 A1 | 10/1995 |
| EP | 0 917 887 A1 | 5/1999 |
| EP | 0 923 130 A1 | 6/1999 |
| EP | 1 000 634 A1 | 5/2000 |
| WO | WO 93/19809 A1 | 10/1993 |
| WO | WO 97/29802 A2 | 8/1997 |
| WO | WO 98/25349 A1 | 6/1998 |
| WO | WO 99/03534 A1 | 1/1999 |
| WO | WO 99/37362 A | 7/1999 |
| WO | WO 99/37362 A1 | 7/1999 |
| WO | WO 99/53991 A1 | 10/1999 |
| WO | WO 00/41766 B1 | 7/2000 |
| WO | WO 00/41766 A1 | 7/2000 |
| WO | WO 00/50120 A1 | 8/2000 |
| WO | WO 01/43649 A1 | 6/2001 |
| WO | WO 01/56166 A2 | 8/2001 |
| WO | WO 02/22208 A2 | 3/2002 |
| WO | WO 02/22208 A3 | 3/2002 |
| WO | WO 02/24275 A | 3/2002 |
| WO | WO 02/24275 A2 | 3/2002 |
| WO | WO 02/24275 A3 | 3/2002 |
| WO | WO 02/068046 A1 | 9/2002 |
| WO | WO 03/018121 A2 | 3/2003 |

OTHER PUBLICATIONS

Schuder, John C. et al., "Experimental Ventricular Defibrillation with an Automatic and Completely Implanted System," *Trans. Amer. Soc. Artif. Int. Organs*, vol. XVI (1970) pp. 207–212.

Schuder, John C. et al., "Standby Implanted Defibrillators," *Arch Intern. Med*, vol. 127, Feb. 1971, p. 317 (single sheet).

Schuder, John C. et al., "Transthoracic Ventricular Defibrillation in the Dog with Truncated and Untruncated Exponential Stimuli," *IEEE Transactions on Bio–Medical Engineering*, vol. BME–18, No. 6, Nov. 1971, pp. 410–415.

Tietze U. et al., "Halbleiter–Schaltungstechnik," ©Springer–Verlag (Berlin, Germany), (1991), pp. 784–786.

Walters, R.A. et al., "Analog to Digital Conversion Techniques in Implantable Devices," *Annual International Conference of the IEEE Engineering in Medicine and Biology Society*, vol. 13, No. 4 (1991) p. 1674–1676.

International Search Report dated Mar. 28, 2003, PCT/IB03/04454 filed Oct. 28, 2002, published as WO 03/041278 on May 15, 2003, "Low Power A/D Converter", Inventors: Ostroff.

International Search Report dated Apr. 16, 2003, PCT/IB03/04546 filed Oct. 28, 2002, published as WO 03/039656 on May 15, 2003, "Subcutaneous Electrode with Improved. Contact Shape for Transthoracic Conduction", Inventors: Bardy et al.

International Search Report dated Apr. 16, 2003 PCT/IB03/04490 filed Oct. 28, 2002, published as WO 03/039665 on May 15, 2003, "Monophasic Waveform for Anti–Tachycardia Pacing for a Subcutaneous Implantable Cardioverter–Defibrillator", Inventors: Cappato.

International Search Report dated Apr. 16, 2003, PCT/IB03/04498 filed Oct. 28, 2002, published as WO 03/039666 on May 15, 2002, "Current Waveforms for Anti–Bradycardia Pacing for a Subcutaneous Implantable Cardioverter–Defibrillator", Inventors: Ostroff et al.

International Search Report dated Apr. 16, 2003, PCT/IB03/04507 filed Oct. 28, 2002, published as WO 03/039667 on May 15, 2003, "Current Waveforms for Anti–Tachycardia Pacing for a Subcutaneous Implantable Cardioverter–Defibrillator", Inventors: Ostroff et al.

International Search Report dated Apr. 16, 2003, PCT/IB03/04516 filed Oct. 28, 2002, published as WO 03/039668 on May 15, 2003, "Flexible Subcutaneous Implantable Cardioverter–Defibrillator", Inventors: Ostroff et al.

International Search Report dated Apr. 16, 2003, PCT/IB03/04543 filed Oct. 28, 2002, published as WO 03/039669 on May 15, 2003, "Monophasic Waveform for Anti–Bradycardia Pacing for a Subcutaneous Implantable Cardioverter–Defibrillator", Inventors: Bardy et al.

International Search Report dated Apr. 23, 2003, PCT/IB02/04497 filed Oct. 28, 2002, published as WO 03/039649 on May 15, 2003, "Packaging Technology For Non–Transvenous Cardioverter–Defibrillator Devices", Inventors: Ostroff et al.

International Search Report dated Apr. 23, 2003, PCT/IB02/04515 filed Oct. 28, 2003, published as WO 03/039651 on May 15, 2003, "Subcutaneous Implantable Cardioverter–Defibrillator Employing A Telescoping Lead", Inventors: Erlinger et al.

International Search Report dated Apr. 25, 2003, PCT/IB02/04475 filed Oct. 28, 2002 published as WO 03/039647 on May 15, 2003, "Optional Use of a Lead For a Unitary Subcutaneous Implantable Cardioverter–Defibrillator", Inventors: Bardy et al.

International Search Report dated May 8, 2003, PCT/IB02/04514 filed Oct. 28, 2002, published as WO 03/039650 on May 15, 2003, "H–Bridge With Sensing Circuit", Inventors: Rissman et al.

International Search Report dated Oct. 1, 2003, PCT/US03/10666 filed Apr. 4, 2003, published as WO 03/089059 on Oct. 30, 2003, "Subcutaneous Cardiac Stimulator Device With Small Contact Surface Electrodes", Inventors: Bardy et al.

International Search Report dated May 8, 2003, PCT/IB02/04476 filed Oct. 28, 2002, published as WO 039648 on May 15, 2003, "Defibrillation Pacing Circuitry", Inventors: Ostroff.

International Preliminary Examination Report dated Nov. 20, 2002; PCT/US01/29168 filed Sep. 14, 2001, published as WO 02/22208 on Mar. 21, 2002, "Subcutaneous Only Implantable Cardioverter Defibrillator Optional Pacer", Inventors: Bardy et al.

International Preliminary Examination Report dated Dec. 18, 2002, PCT/US01/29106 filed Sep. 14, 2001, published as WO 02/24275 on Mar. 28, 2002, "Subcutaneous Only Implantable Cardioverter Defibrillator & Optional Pacer", Inventors: Bardy et al.

International Preliminary Examination Report dated Sep. 2, 2003, PCT/IB02/03447 filed Aug. 27, 2002; published as WO 03/018110 on Mar. 6, 2003, "Subcutaneous Electrode for Transthoracic Conduction with Improved Installation Characteristics", Inventors: Bardy et al.

International Preliminary Examination Report dated Sep. 9, 2003, PCT/IB02/03452 filed Aug. 23, 2002; published as WO 03/018119 on Mar. 6, 2003, "Insulated Shell for Subscutaneously Implantable Cardioverter–Defibrillator Canister", Inventors Bardy et al.

International Preliminary Examination Report dated Sep. 2, 2003, PCT/IB02/03453 filed Aug. 23, 2002; published as WO 03/018122 on Mar. 6, 2003, "Duckbill–Shaped Implantable Cardioverter–Defibrillator Canister and Method of Use", Inventors: Bardy et al.

International Preliminary Examination Report dated Sep. 2, 2003, PCT/IB02/03467 filed Aug. 26, 2002; published as WO 03/018123 on Mar. 6, 2003, "Canister Designs for Implantable Cardioverter–Defibrillators", Inventors: Bardy et al.

International Preliminary Examination Report dated Sep. 2, 2003, PCT/IB02/03469 filed Aug. 26, 2002; published as WO 03/018124 on Mar. 6, 2003, "Biphasic Waveform for a Subcutaneous Implantable Cardioverter–Defibrillator", Inventors: Bardy et al.

International Preliminary Examination Report dated Sep. 2, 2003, PCT/IB02/03484 filed Aug. 26, 2002; published as WO 03/018126 on Mar. 6, 2003, "Cardioverter–Defibrillator having a Focused Shocking Area and Orientation Thereof", Inventors: Bardy et al.

International Preliminary Examination Report dated Sep. 2, 2003, PCT/IB02/03501 filed Aug. 26, 2002; published as WO 03/018112 on Mar. 6, 2003, "Subcutaneous Electrode for Transthoracic Conduction with Low–Profile Installation Appendage and Method of Doing Same", Inventors Bardy et al.

International Preliminary Examination Report dated Sep. 2, 2003, PCT/IB02/03502 filed Aug. 23, 2002; published as WO 03/018127 on Mar. 6, 2003, "Subcutaneous Electrode for Transthoracic Conduction with Insertion Tool", Inventors: Bardy et al.

International Preliminary Examination Report dated Sep. 2, 2003, PCT/IB02/03503 filed Aug. 26, 2002; published as WO 03/018128 on Mar. 6, 2003, "Power Supply for a Subcutaneous Implantable Cardioverter–Defibrillator", Inventors: Bardy et al.

International Preliminary Examination Report dated Sep. 2, 2003, PCT/IB02/03522 filed Aug. 26, 2002; published as WO 03/018129 on Mar. 6, 2003, "Biphasic Waveform for Anti–Bradycardia Pacing for a Subcutaneous Implantable Cardioverter–Defibrillator", Inventors: Bardy et al.

International Preliminary Examination Report dated Sep. 2, 2003, PCT/IB02/03525 filed Aug. 23, 2002; published as WO 03/018130 on Mar. 6, 2003, "Subcutaneous Electrode for Transthoracic Conduction with Highly Maneuverable Insertion Tool", Inventors: Bardy et al.

International Preliminary Examination Report dated Sep. 2, 2003, PCT/IB02/03488 filed Aug. 26, 2002, published as WO 03/018120 on Mar. 6, 2003, "Curved Implantable Cardioverter–Defibrillator Canister", Inventors: Bardy et al.

Written Opinion dated May 12, 2003, PCT/IB02/03447 filed Aug. 27, 2002; published as WO 03/018110 on Mar. 6, 2003, "Subcutaneous Electrode for Transthoracic Conduction with Improved Installation Characteristics", Inventors: Bardy et al.

Written Opinion dated May 12, 2003, PCT/IB02/03452 filed Aug. 23, 2002; published as WO 03/018119 on Mar. 6, 2003, "Insulated Shell for Subcutaneously Implantable Cardioverter–Defibrillator Canister", Inventors Bardy et al.

Written Opinion dated May 12, 2003, PCT/IB02/03453 filed Aug. 23, 2002; published as WO 03/018122 on Mar. 6, 2003, "Duckbill–Shaped Implantable Cardioverter–Defibrillator Canister and Method of Use", Inventors: Bardy et al.

Written Opinion dated May 12, 2003, PCT/IB02/03467 filed Aug. 26, 2002; published as WO 03/018123 on Mar. 6, 2003, "Canister Designs for Implantable Cardioverter–Defibrillators", Inventors: Bardy et al.

Written Opinion dated May 12, 2003, PCT/IB02/03469 filed Aug. 26, 2002; published as WO 03/018124 on Mar. 6, 2003, "Biphasic Waveform for a Subcutaneous Implantable Cardioverter–Defibrillator", Inventors: Bardy et al.

Written Opinion dated May 12, 2003, PCT/IB02/03484 filed Aug. 26, 2002; published as WO 03/018126 on Mar. 6, 2003, "Cardioveter–Defibrillator having a Focused Shocking Area and Orientation Thereof", Inventors: Bardy et al.

Written Opinion dated May 12, 2003, PCT/IB02/03502 filed Aug. 23, 2002; published as WO 03/018127 on Mar. 6, 2003, "Subcutaneous Electrode for Transthoracic Conduction with Insertion Tool", Inventors: Bardy et al.

Written Opinion dated May 12, 2003, PCT/IB02/03503 filed Aug. 26, 2002; published as WO 03/018128 on Mar. 6, 2003, "Power Supply for a Subcutaneous Implantable Cardioverter–Defibrillator", Inventors: Bardy et al.

Written Opinion dated May 12, 2003, PCT/IB02/03522 filed Aug. 26, 2002; published as WO 03/018129 on Mar. 6, 2003, "Biphasic Waveform for Anti–Bradycardia Pacing for a Subcutaneous Implantable Cardioverter–Defibrillator", Inventors: Bardy et al.

Written Opinion dated May 12, 2003, PCT/IB02/03525 filed Aug. 23, 2002; published as WO 03/018130 on Mar. 6, 2003, "Subcutaneous Electrode for Transthoracic Conduction with Highly Maneuverable Insertion Tool", Inventors: Bardy et al.

Written Opinion dated May 12, 2003, PCT/IB02/03488 filed Aug. 26, 2002, published as WO 03/018120 on Mar. 6, 2003, "Curved Implantable Cardioverter–Defibrillator Canister", Inventors: Bardy et al.

IEEE Engineering in Medicine & Biology Society Magazine—Proceedings of the Annual International Conference of the IEEE Orlando, FL, copyright 1991, vol. 13, 1674–1676 pp, "Analog to Digital Conversion Techniques in Implantable Devices", by RA Walters et al Comment s on Relevance: ISR PCT/IB03/04454.

Pace, vol. 16, Part I, Jan. 1993, 95–124pp, "The Role Of An Engineering Oriented Medical Research Group in Developing Improved Methods & Devices For Achieving Ventricular Defibrillation: The University of Missouri Experience", by JC Schuder PhD.

Springer–Verlag, Berlin–Germany, copyright 1991, 784–786pp, "Halbleiter–Schaltungstechnik", by U. Tietze and Ch. Schenk Comments on Relevance: ISR PCT/IB03/04454.

"Onset & Stability for Ventricular Tachyarrhythmia Detection in an Implantable Pacer–Cardioverter–Defibrillator", IEEE Computers in Cardiology, 1987, vol 0276–6574, 167–170pp, by Walter H Olson et al.

U.S. patent application Ser. No. 09/663,606, Bardy et al.

U.S. patent application Ser. No. 09/663,607, Bardy et al.

International Search Report dated Mar. 26, 2002, PCT/US01/29168 filed Sep. 14, 2001, published as WO 02/22208 on Mar. 21, 2002, Subcutaneous Only Implantable Cardioverter Defibrillator & Optional Pacer, Inventors: Gust H Bardy et al.

Written Opinion dated Sep. 10, 2002, PCT/US01/29168 filed Sep. 14, 2001, published as WO 02/22208 on Mar 21, 2002, Subcutaneous Only Implantable Cardioverter Defibrllillator & Optional Pacer, Inventors: Gust H Brady et al.

International Search Report dated Mar. 21, 2002, PCT/US01/29106 filed Sep. 14, 2001, published as WO 02/24275 on Mar. 28, 2002, Unitary Subcutaneous Only Implantable Cardioverter Defibrillator & Optional Pacer, Inventors: Gust H Bardy et al.

Written Opinion dated Sep. 3, 2002, PCT/US01/29106 filed Sep. 14, 2001, published as WO 02/24275 on Mar. 28, 2002, Unitary Subcutaneous Only Implantable Cardioverter Defibrillator & Optional Pacer, Inventors: Gust H Bardy et al.

International Search Report dated Feb. 14, 2003, PCT/IB02/03452 filed Aug. 23, 2002; Not yet published; Applicant: Cameron Health Inc.

International Search Report dated Feb. 14, 2003, PCT/IB02/03453 filed Aug. 23, 2002; Not yet published; Applicant: Cameron Health Inc.

International Search Report dated Feb. 14, 2003, PCT/IB02/03467 filed Aug. 26, 2002; Not yet published; Applicant: Cameron Health Inc.

International Search Report dated Feb. 14, 2003, PCT/IB02/03469 filed Aug. 26, 2002; Not yet published; Applicant: Cameron Health Inc.

International Search Report dated Feb. 14, 2003, PCT/IB02/03484 filed Aug. 26, 2002; Not yet published; Applicant: Cameron Health Inc.

International Search Report dated Feb. 14, 2003, PCT/IB02/03488 filed Aug. 26, 2002; Not yet published; Applicant: Cameron Health Inc.

International Search Report dated Feb. 14, 2003, PCT/IB02/03522 filed Aug. 26, 2002; Not yet published; Applicant: Cameron Health Inc.

International Search Report dated Feb. 18, 2003, PCT/IB02/03503 filed Aug. 26, 2002; Not yet published; Applicant: Cameron Health Inc.

International Search Report dated Feb. 20, 2003, PCT/IB02/03447 filed Aug. 27, 2002; Not yet published; Applicant: Cameron Health Inc.

International Search Report dated Feb. 20, 2003, PCT/IB02/03481 filed Aug. 28, 2002; Not yet published; Applicant: Cameron Health Inc.

International Search Report dated Feb. 20, 2003, PCT/IB02/03501 filed Aug. 26, 2002; Not yet published; Applicant: Cameron Health Inc.

International Search Report dated Feb. 20, 2003, PCT/IB02/03502 filed Aug. 23, 2003; Not yet published; Applicant: Cameron Health Inc.

International Search Report dated Feb. 20, 2003, PCT/IB02/03525 filed Aug. 23, 2002; Not yet published; Applicant: Cameron Health Inc.

International Search Report dated Mar. 6, 2003, PCT/IB02/04513 filed Oct. 28, 2003; Not yet published; Applicant: Cameron Health Inc.

Office Action dated Oct. 15, 2002; U.S. patent application Ser. No. 09/663,606; Inventors: Bardy et al.

Journal of the American Medical Association (JAMA), vol. 214, No. 6, 1123pp, Nov. 9, 1970, "Completely Implanted Defibrillator", an editorial comment by JC Schuder PhD.

Amer Soc Trans Artif Int Organs, vol. XVI, 1970, 207–212pp, "Experimental Ventricular Defibrillation With An Automatic & Completely Implanted System", by JC Schuder PhD et al.

Archives of Internal Medicine (Specialized Journal of the AMA), vol. 127, Feb. 1971, Letters to the Editor pp 317, "Standby Implanted Defibrillators", an editirial comment by JC Schuder PhD.

Journal of the American Medical Association (JAMA), vol. 213, 615–616pp, 1970, "Automatic Detection & Defibrillation of Lethal Arrhythmias—A New Concept", by Mirkowski et al.

IEEE Transactions on Bio–Medical Engineering, vol. BME–18, No. 6, Nov. 1971, 410–415pp, "Transthoracic Ventricular Defibrillation In The Dog With Truncated and Untruncated Exponential Stimuli", by JC Schuder PhD et al.

Pace, vol. 16, Part I, Jan. 1993, pp 95–124, "The Role Of An Engineering Oriented Medical Research Group In Developing Improved Methods & Devices For Achieving Ventricular Defibrillation: The University of Missouri Experience", by JC Schuder PhD.

Journal of Cardiovascular Electrophysiology, vol. 12, No. 3, Mar. 2001, pp 356–360, Copyright 2001, by Future Publishing Company Inc, Armonk–NY 1050–0418, "Nonthoracotomy Implantable Cardioverter Defibrillator Placement In Children", by Rainer Gradaus MD et al.

Journal of Cardiovascular Electrophysiology, vol. 12, No. 3, Mar. 2001, 361–362pp, Copyright 2001, by Future Publishing Company Inc, Armonk–NY 1050–0418, "Implantable Defibrillators In Children: From Whence to Shock", by Richard A Friedman MD et al.

* cited by examiner

SWITCHED CAPACITOR DEFIBRILLATION CIRCUIT

CROSS-REFERENCE TO RELATED APPLICATIONS

The present invention may find application in systems such as are disclosed in the U.S. patent application entitled "SUBCUTANEOUS ONLY IMPLANTABLE CARDIOVERTER-DEFIBRILLATOR AND OPTIONAL PACER," having Ser. No. 09/663,607, filed Sep. 18, 2000, pending, and U.S. patent application entitled "UNITARY SUBCUTANEOUS ONLY IMPLANTABLE CARDIOVERTER-DEFIBRILLATOR AND OPTIONAL PACER," having Ser. No. 09/663,606, filed Sep. 18, 2000, pending, of which both applications are assigned to the assignee of the present application, and the disclosures of both applications are hereby incorporated by reference.

Applications related to the foregoing applications include a U.S. patent application entitled "DUCKBILL-SHAPED IMPLANTABLE CARDIOVERTER-DEFIBRILLATOR AND METHOD OF USE," U.S. patent application entitled "CERAMICS AND/OR OTHER MATERIAL INSULATED SHELL FOR ACTIVE AND NON-ACTIVE S-ICD CAN," U.S. patent application entitled "SUBCUTANEOUS ELECTRODE FOR TRANSTHORACIC CONDUCTION WITH IMPROVED INSTALLATION CHARACTERISTICS," U.S. patent application entitled "SUBCUTANEOUS ELECTRODE WITH IMPROVED CONTACT SHAPE FOR TRANSTHORACIC CONDUCTION," U.S. patent application entitled "SUBCUTANEOUS ELECTRODE FOR TRANSTHORACIC CONDUCTION WITH HIGHLY MANEUVERABLE INSERTION TOOL," U.S. patent application entitled "SUBCUTANEOUS ELECTRODE FOR TRANSTHORACIC CONDUCTION WITH LOW-PROFILE INSTALLATION APPENDAGE AND METHOD OF DOING SAME," U.S. patent application entitled "SUBCUTANEOUS ELECTRODE FOR TRANSTHORACIC CONDUCTION WITH INSERTION TOOL," U.S. patent application entitled "METHOD OF INSERTION AND IMPLANTATION FOR IMPLANTABLE CARDIOVERTER-DEFIBRILLATOR CANISTERS," U.S. patent application entitled "CANISTER DESIGNS FOR IMPLANTABLE CARDIOVERTER-DEFIBRILLATORS," U.S. patent application entitled "RADIAN CURVED IMPLANTABLE CARDIOVERTER-DEFIBRILLATOR CANISTER," U.S. patent application entitled "CARDIOVERTER-DEFIBRILLATOR HAVING A FOCUSED SHOCKING AREA AND ORIENTATION THEREOF," U.S. patent application entitled "BIPHASIC WAVEFORM FOR ANTI-BRADYCARDIA PACING FOR A SUBCUTANEOUS IMPLANTABLE CARDIOVERTER-DEFIBRILLATOR," and U.S. patent application entitled "BIPHASIC WAVEFORM FOR ANTI-TACHYCARDIA PACING FOR A SUBCUTANEOUS IMPLANTABLE CARDIOVERTER-DEFIBRILLATOR," the disclosures of which applications are hereby incorporated by reference.

FIELD OF THE INVENTION

The subject invention relates to electronic circuitry and particularly to circuitry having applications in defibrillating apparatus.

BACKGROUND OF THE INVENTION

Defibrillation/cardioversion is a technique employed to counter arrhythmic heart conditions including some tachycardias in the atria and/or ventricles. Typically, electrodes are employed to stimulate the heart with electrical impulses or shocks, of a magnitude substantially greater than pulses used in cardiac pacing. Because current density is a key factor in both defibrillation and pacing, implantable devices may improve what is capable with the standard waveform where the current and voltage decay over the time of pulse deliver. Consequently, a waveform that maintains a constant current over the duration of delivery to the myocardium may improve defibrillation as well as pacing.

Defibrillation/cardioversion systems include body implantable electrodes that are connected to a hermetically sealed container housing the electronics, battery supply and capacitors. The entire system is referred to as implantable cardioverter/defibrillators (ICDs). The electrodes used in ICDs can be in the form of patches applied directly to epicardial tissue, or, more commonly, are on the distal regions of small cylindrical insulated catheters that typically enter the subclavian venous system, pass through the superior vena cava and, into one or more endocardial areas of the heart. Such electrode systems are called intravascular or transvenous electrodes. U.S. Pat. Nos. 4,603,705, 4,693,253, 4,944,300, 5,105,810, the disclosures of which are all incorporated herein by reference, disclose intravascular or transvenous electrodes, employed either alone, in combination with other intravascular or transvenous electrodes, or in combination with an epicardial patch or subcutaneous electrodes. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat No. 5,476,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of a pulse monitor/generator surgically implanted into the abdomen and subcutaneous electrodes implanted in the thorax. This system is far more complicated to use than current ICD systems using transvenous lead systems together with an active can electrode and therefore it has no practical use. It has in fact never been used because of the surgical difficulty of applying such a device (3 incisions), the impractical abdominal location of the generator and the electrically poor sensing and defibrillation aspects of such a system.

Recent efforts to improve the efficiency of ICDs have led manufacturers to produce ICDs which are small enough to be implanted in the pectoral region. In addition, advances in circuit design have enabled the housing of the ICD to form a subcutaneous electrode. Some examples of ICDs in which the housing of the ICD serves as an optional additional electrode are described in U.S. Pat. Nos. 5,133,353, 5,261, 400, 5,620,477, and 5,658,321 the disclosures of which are incorporated herein by reference.

ICDs are now an established therapy for the management of life threatening cardiac rhythm disorders, primarily ventricular fibrillation (V-Fib). ICDs are very effective at treating V-Fib, but are therapies that still require significant surgery.

As ICD therapy becomes more prophylactic in nature and used in progressively less ill individuals, especially children at risk of cardiac arrest, the requirement of ICD therapy to use intravenous catheters and transvenous leads is an impediment to very long term management as most individuals will begin to develop complications related to lead system malfunction sometime in the 5–10 year time frame, often earlier. In addition, chronic transvenous lead systems, their reimplantation and removals, can damage major cardiovascular venous systems and the tricuspid valve, as well as result in life threatening perforations of the great vessels and heart. Consequently, use of transvenous lead systems, despite their many advantages, are not without their chronic patient management limitations in those with life expectancies of >5 years. The problem of lead complications is even greater in children where body growth can substantially alter transvenous lead function and lead to additional cardiovascular problems and revisions. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of a related therapy, the automatic external defibrillator (AED). AEDs employ the use of cutaneous patch electrodes, rather than implantable lead systems, to effect defibrillation under the direction of a bystander user who treats the patient suffering from V-Fib with a portable device containing the necessary electronics and power supply that allows defibrillation. AEDs can be nearly as effective as an ICD for defibrillation if applied to the victim of ventricular fibrillation promptly, i.e., within 2 to 3 minutes of the onset of the ventricular fibrillation.

AED therapy has great appeal as a tool for diminishing the risk of death in public venues such as in air flight. However, an AED must be used by another individual, not the person suffering from the potential fatal rhythm. It is more of a public health tool than a patient-specific tool like an ICD. Because >75% of cardiac arrests occur in the home, and over half occur in the bedroom, patients at risk of cardiac arrest are often alone or asleep and can not be helped in time with an AED. Moreover, its success depends to a reasonable degree on an acceptable level of skill and calm by the bystander user.

What is needed therefore, especially for children and for prophylactic long term use for those at risk of cardiac arrest, is a combination of the two forms of therapy which would provide prompt and near-certain defibrillation, like an ICD, but without the long-term adverse sequelae of a transvenous lead system while simultaneously using most of the simpler and lower cost technology of an AED. What is also needed is a cardioverter/defibrillator that is of simple design and can be comfortably implanted in a patient for many years.

Moreover, it has appeared advantageous to the inventor to provide the capability in such improved circuitry to produce a defibrillating waveform which includes a defibrillating pulse approximating a rectangular pulse. Such a pulse is advantageous, for example, because it can approximate a constant current density across the heart.

SUMMARY

According to the invention, circuitry is provided for enabling the generation of an approximation of a rectangular waveform from energy stored in energy storage devices such as a capacitor.

BRIEF DESCRIPTION OF THE DRAWINGS

For a better understanding of the invention, reference is now made to the drawings where like numerals represent similar objects throughout the figures and wherein.

DETAILED DESCRIPTION OF ILLUSTRATIVE EMBODIMENTS

Figure 1:
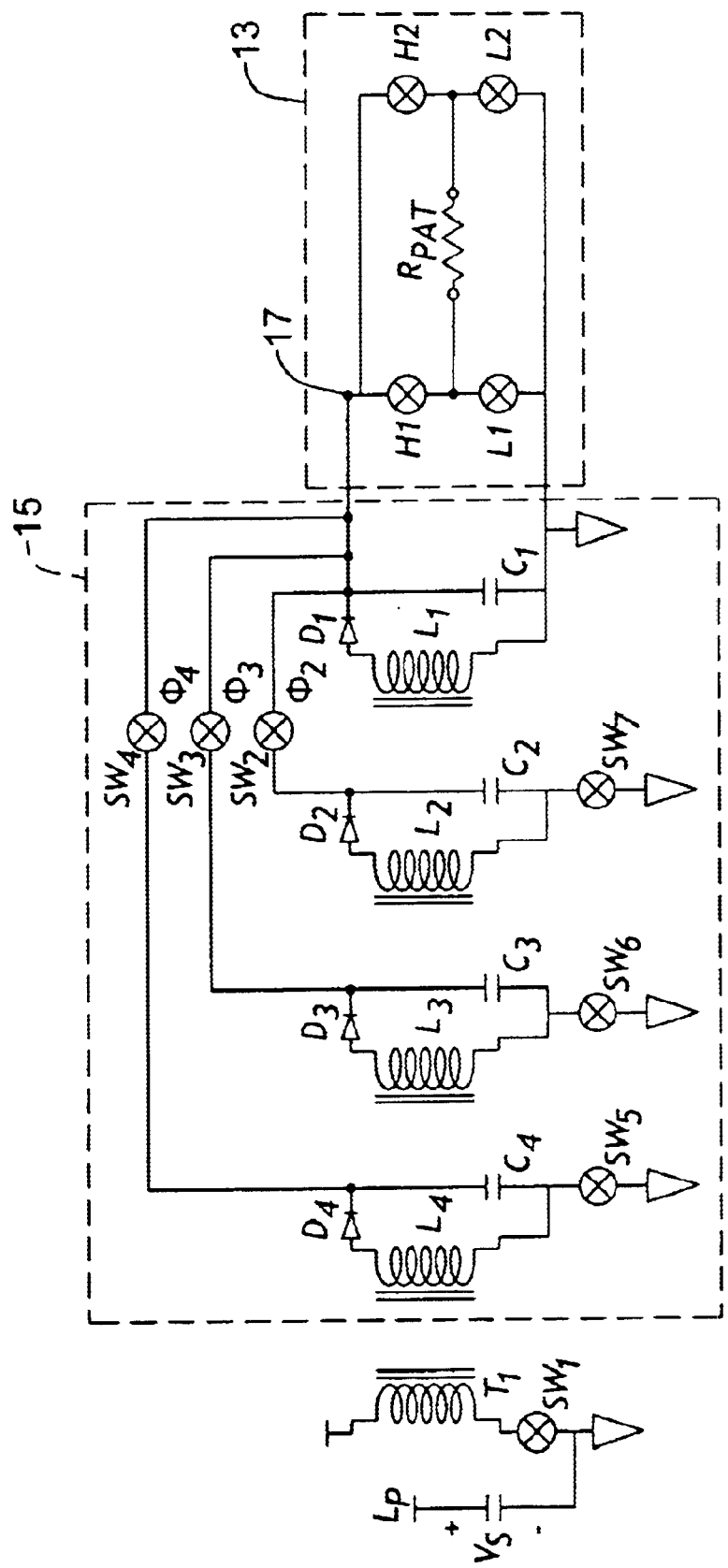
FIG. 1 is an electrical circuit schematic of an illustrative embodiment of the invention.

An illustrative embodiment is shown in FIG. 1. The illustrative embodiment includes an H bridge circuit 13 and a drive circuit 15 for supplying voltage or energy to the H bridge circuit 13.

The H bridge circuit 13 may be of conventional form, including first and second high side switches $H_1$, $H_2$ and first and second low side switches $L_1$, $L_2$. The switches $H_1$, $H_2$; $L_1$, $L_2$ may be manipulated to appropriately and selectively apply a voltage present at junction 17 across a patient indicated by a patient resistance $R_{PAT}$. The H bridge circuit 13 may also include features disclosed in co-pending applications filed herewith on behalf of inventor Alan H. Ostroff and entitled Defibrillation Pacing Circuitry and Simplified Defibrillator Output Circuit.

The drive circuit 15 of FIG. 1 includes a plurality of energy storage devices in the illustrative form of four capacitors $C_1$, $C_2$, $C_3$, $C_4$. Across each capacitor $C_1$, $C_2$, $C_3$, $C_4$ is connected a respective secondary $l_1$, $l_2$, $l_3$, $l_4$ of a transformer $T_1$. The primary of the transformer $T_1$ is switchable via a switch $SW_1$ to connect to a source of D.C. voltage $V_S$, e.g., a battery.

The first capacitor $C_1$ has a first terminal connected to ground and a second terminal in common with the junction 17. The second terminal of the capacitor $C_1$ is further connected to the cathode of a diode $D_1$, whose anode is connected to a first terminal of the first secondary winding $l_1$. The remaining capacitors $C_2$, $C_3$, $C_4$ have second terminals which are switchable via respective switches $SW_2$, $SW_3$, $SW_4$ to establish or remove electrical connection to the junction 17. The respective first terminals of the capacitors $C_2$, $C_3$, $C_4$ are connected to respective switches $SW_5$, $SW_6$, $SW_7$ which can be selectively operated to connect those respective first terminals to ground. The respective second terminals of the capacitors $C_2$, $C_3$, $C_4$ are connected to the respective cathodes of respective diodes $D_2$, $D_3$, $D_4$. The respective anodes of the diodes $D_2$, $D_3$, $D_4$ are connected to respective first terminals of the secondary windings $l_2$, $l_3$, $l_4$, whose second terminals are connected to ground.

In illustrative operation of the circuit of FIG. 1, the capacitors $C_1$, $C_2$, $C_3$, $C_4$ are charged to a common voltage level V. Next, the high side switch $H_1$ and the low side switch $L_2$ are closed while $H_2$ and $L_1$ are open, thereby connecting the voltage on the capacitor $C_1$ across the patient resistance $R_{PAT}$.

Figure 2:
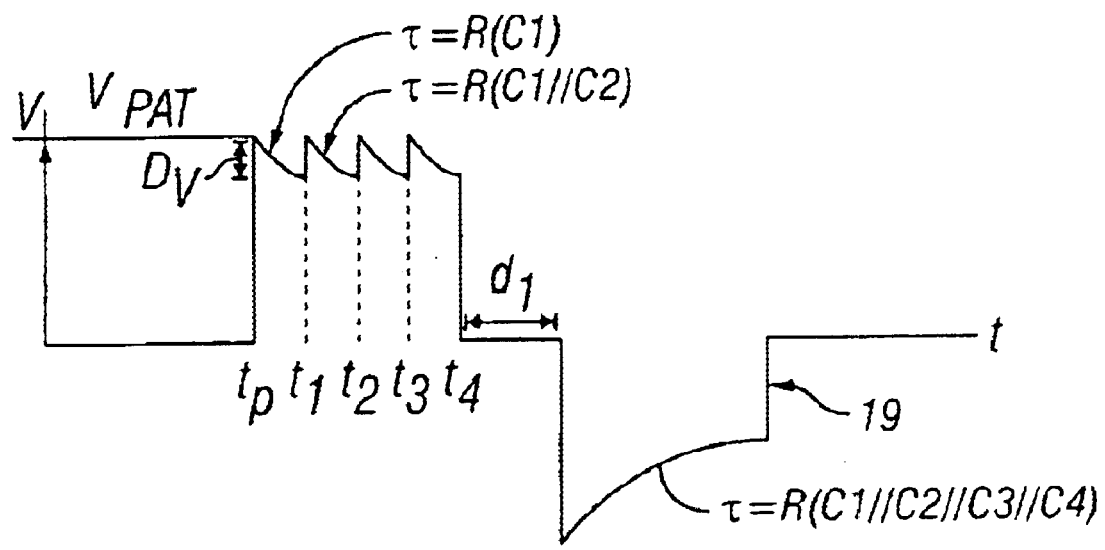
FIG. 2 is a waveform diagram illustrative of operation of the circuit of FIG. 1.
Figure 3:
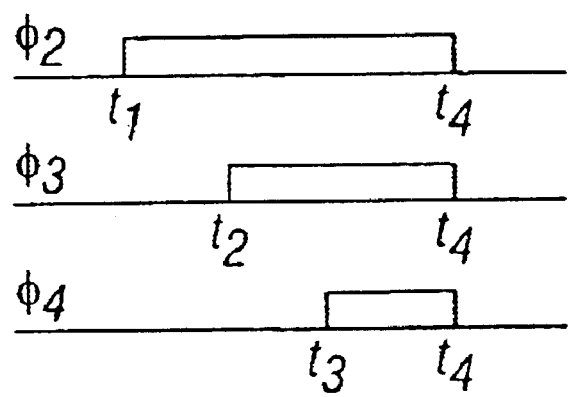
FIG. 3 is a waveform diagram illustrative of operation of the circuit of FIG. 1.

As shown in FIG. 2, the voltage across the patient is initially $V_{PAT}$ and decays with a time constant $RC_1$ for a selected time period up to a point in time denoted $t_1$ in FIG. 2. At time $t_1$, a switching signal $\Phi_2$ (FIG. 3) is activated to close the switch $SW_2$. The patient voltage $V_{PAT}$ initially rises and then begins to decay with time constant equal to $R(C_1+C_2)$. At a selected time $t_2$, a switching signal $\Phi_3$ is activated, closing the switch $SW_3$ and connecting the voltage across the capacitor $C_3$ to the junction 17. As shown in FIG. 2, the patient voltage again rises and thereafter begins to decay with a time constant equal to $R(C_1+C_2+C_3)$. Then, at time $t_3$, the switching signal $\Phi_4$ is activated, closing the switch $SW_4$, thereby applying the voltage across the capacitor $C_4$ and to the junction 17, again resulting in the voltage $V_{PAT}$ rising and thereafter decaying with a time constant $R(C_1+C_2+C_3+C_4)$. Finally, at time $t_4$, the switches $H_1$, $L_2$ are opened, thereby terminating the first phase of the waveform.

If desired, these switches $H_2$, $L_1$ may then be closed to produce a conventional second phase 19 of a biphasic waveform. This waveform drops to a voltage $V_{PAT1}$ and then decays with a time constant determined by the patient resistance $R_{PAT}$ and the effective value of the parallel capacitors $C_1$, $C_2$, $C_3$, $C_4$. An inverted biphasic waveform may also be produced by first activating $H_2$ and $L_1$.

It will be observed that circuitry according to the preferred embodiment produces an approximation to a square or rectangular pulse. The times $t_1$, $t_2$, $t_3$, $t_4$ can easily be adjusted to further control the shape of the waveform, for example, such that $\Delta V$ remains constant for each interval of decay despite the change in time constants each time an additional capacitor, e.g., $C_2$, $C_3$, $C_4$, is switched into the current. Additionally, the number of parallel capacitors, e.g., $C_1$, $C_2$, $C_3$, etc., may be more or less than the number depicted in FIG. 1, a particularly useful range being two to seven.

While the present invention has been described above in terms of specific embodiments, it is to be understood that the invention is not limited to the disclosed embodiments. On the contrary, the following claims are intended to cover various modifications and equivalent methods and structures included within the spirit and scope of the invention.

What is claimed is:

1. An apparatus comprising:

first and second switches adapted to be connected across a patient resistance and activatable when so connected to deliver a current to said patient in response to switching signals activating said first and second switches;

a plurality of capacitors providing said current through said first and second switches; and capacitor switch means for selectively coupling said plurality of capacitors into parallel relation with one another to generate an approximate rectangular waveform for said current;

wherein said capacitor switch means and said plurality of capacitors cooperate to cause said waveform to rise to a first voltage level, decay for a selected time interval and thereafter experience a second rise and decay for a second selected time interval; and wherein said plurality of capacitors includes a first and a second capacitor and said second rise and second delay are caused by said capacitor switch means switching of the second capacitor into parallel connection with the first capacitor.

2. The apparatus of claim 1 wherein said capacitor switch means includes a plurality of additional switches selectively activated to create said parallel connection.

3. An apparatus comprising:

first and second switches adapted to be connected across a patient resistance and activatable when so connected to deliver a current to said patient in response to switching signals activating said first and second switches;

a plurality of capacitors providing said current through said first and second switches; and capacitor switch means for selectively coupling said plurality of capacitors into parallel relation with one another to generate an approximate rectangular waveform for said current;

wherein said capacitor switch means and said plurality of capacitors cooperate to cause said waveform to rise to a first voltage level, decay for a selected time interval and thereafter experience a second rise and decay for a second selected time interval;

wherein said plurality of capacitors includes at least four capacitors and said capacitor switch means includes a plurality of additional switches, said additional switches being constructed and arranged to selectively couple said capacitors into one of a plurality of parallel combinations; and wherein said capacitors are selectively coupled in sequence to generate said waveform with four respective decays, said decays being proportional respectively to $C_1$, $C_1+C_2$, $C_1+C_2+C_3$, $C_1+C_2+C_3+C_4$ where $C_1$, $C_2$, $C_3$, and $C_4$ represent the respective values of said four capacitors.

4. The apparatus of claim 3 further comprising transformer windings, an energy source coupled to said transformer windings and coupling means for coupling said plurality of capacitors to said transformer windings to charge said capacitors to a predetermined voltage.

* * * * *